United States Patent
Kawaguchi et al.

(10) Patent No.: US 6,348,326 B1
(45) Date of Patent: Feb. 19, 2002

(54) PROCESS FOR PRODUCING L-RIBOSE

(75) Inventors: Tomoko Kawaguchi; Mari Hara; Makoto Ueda, all of Yokohama (JP)

(73) Assignee: Mitsubishi Chemical Corporation, Tokyo (JP)

(*) Notice: Subject to any disclaimer, the term of this patent is extended or adjusted under 35 U.S.C. 154(b) by 0 days.

(21) Appl. No.: 09/701,178

(22) PCT Filed: May 27, 1999

(86) PCT No.: PCT/JP99/02793
§ 371 Date: Nov. 27, 2000
§ 102(e) Date: Nov. 27, 2000

(87) PCT Pub. No.: WO99/61648
PCT Pub. Date: Dec. 2, 1999

(30) Foreign Application Priority Data

May 27, 1998 (JP) ............................................. 10-145548

(51) Int. Cl.$^7$ .......................... C12P 39/00; C12P 19/24; C12P 19/02
(52) U.S. Cl. ............................ 435/42; 435/94; 435/105
(58) Field of Search ............................ 435/42, 105, 94

(56) References Cited

U.S. PATENT DOCUMENTS 3,669,845 A    6/1972   Imai et al.

FOREIGN PATENT DOCUMENTS

| CS | 197528 | 5/1980 |
|---|---|---|
| EP | 0136802 | 4/1985 |
| EP | 0136803 | 4/1985 |
| EP | 0136804 | 4/1985 |
| EP | 0136805 | 4/1985 |
| EP | 0807682 | 11/1997 |
| EP | 807682 | 11/1997 |
| EP | 1041140 | 10/2000 |
| JP | 44-16350 | 7/1969 |
| JP | 45-2071 | 1/1970 |
| JP | 49-12718 | 3/1974 |
| JP | 11-18792 | 1/1999 |
| JP | 11-137285 | 5/1999 |
| WO | 98/23766 | 6/1998 |
| WO | 98/23766 | 8/1998 |
| WO | 99/33953 | 7/1999 |

OTHER PUBLICATIONS

Shimonishi T., "A new enzyme, L–ribose isomerase from acinetobacter sp. strain DL–28", J. Ferment. Bioeng. 81 [6] (1996), pp. 493–497.

Bhuiyan H.S., et al., "A new method for the production of L–lyxose from ribitol using microbial and enzymatic reactions", J. Ferment. Bioeng. 86 [5] (Nov. 1998), pp. 513–516.

Arcus et al., "Polyol Dehydrogenases", Biochem. J., vol. 64, pp. 385–394(1956).

Horecker, "L–Ribulose and L–Arabinose", Methods Enzym. Anal. (3$^{rd}$ Ed.) (1984) vol. 6, pp. 442–449.

Shimonishi T., et al., "A new enzyme, L–ribose isomerase from acinetobacter sp. strain DL–28", J. Ferment. Bioeng. 81 [6] (1996), pp. 493–497.

Bhuiyan H.S., et al., "A new method for the production of L–lyxose from ribitol using microbial and enzymatic reactions", J. Ferment. Bioeng. 86 [5] (Nov. 1998), pp. 513–516.

*Primary Examiner*—Herbert J. Lilling
(74) *Attorney, Agent, or Firm*—Wenderoth, Lind & Ponack, L.L.P.

(57) ABSTRACT

L-Ribose is produced by the steps of producing ribitol from a saccharide raw material by using a microorganism having an ability to produce ribitol from a saccharide raw material, producing L-ribulose from the ribitol by using a microorganism having an ability to produce L-ribulose from ribitol, and producing L-ribose from the L-ribulose by using a microorganism having an ability to produce L-ribose from L-ribulose.

25 Claims, No Drawings

PROCESS FOR PRODUCING L-RIBOSE

CROSS-REFERENCE

This application is a 371 of PCT/JP99/02793 filed May 27, 1999.

TECHNICAL FIELD

The present invention relates to a method for producing L-ribose by multiple steps of biological reactions starting from an inexpensive saccharide.

RELATED ART

In recent years, non-naturally occurring saccharides attracts attention as intermediate materials of pharmaceutical drugs and agricultural chemicals. As for ribose, almost no prospect can be currently seen for supply of the non-naturally occurring L-isomer, in spite of the fact that naturally occurring D-isomer is abundantly distributed all over the living world not only as the constitutional saccharide of DNA as a matter of course, but also as the constitutional saccharide of various vitamins or coenzymes. As the major method for producing L-ribose known at present, the synthetic method starting from L-arabinose as the raw material and utilizing a cobalt catalyst can be mentioned. On the other hand, as for a method for producing L-ribose using a microorganism, there is only one report that an enzyme produced by Acinetobacter calcoaceticus DL-28 strain isomerizes L-ribulose to produce L-ribose (Journal of Fermentation and Bioengineering Vol. 81, No. 6, 493–497, 1996).

As methods for producing L-ribulose, which is the raw material of the aforementioned enzymatic reaction, there are known a method utilizing isomerization of L-arabinose by L-arabinose isomerase (Methods Enzym. Anal. (3rd Ed.) vol. 6, 442–449, 1984) and a method utilizing a microbial reaction starting from purified ribitol as the starting material (Biochem. J., vol. 64, 385, 1956). However, it is hard to say for the both methods that the raw materials of L-arabinose and ribitol are inexpensive, and there has not been reported any process for stably supplying L-ribulose in an industrial scale.

As microbiological production methods of ribitol, which is the raw material used in one of the aforementioned two kinds of methods for producing L-ribulose, there have been reported production methods by an enzymatic reaction using D-ribose as a raw material (Japanese Patent Publication Nos. 45-2071/1972 and 49-12718/1974), production methods by fermentation of glucose etc. (Japanese Patent Publication Nos. 6-30591/1988, 6-30592/1988, 6-30593/1988, 6-30594/1988) and a production method by carbon dioxide fixation of an algae (Japanese Patent Publication No. 44-16350/1969).

However, any combination of the aforementioned techniques could not produce L-ribose in an industrial scale, and therefore no technique is known at all for producing L-ribose in an industrial scale as well as isolating and purifying L-ribose with high purity and high yield from the produced solution containing L-ribose.

In fact, when it is attempted to biologically produce L-ribose in an industrial scale using a conventional method, various problems arise. That is, for the first step, i.e., the production of ribitol, a method by fermentation of an inexpensive raw material such as the glucose is desirable among the conventional methods. However, such a conventional method cannot necessarily provide satisfactory productivity of ribitol even though it can efficiently produce sugar alcohols such as erythritol.

As for the technique for the second step, i.e., the conversion of ribitol into L-ribulose, in conventional methods, ribitol as the raw material must be purified. However, crystallized ribitol is very expensive as the raw material. Moreover, when the aforementioned fermented ribitol is used, it contains a large amount of polyalcohols such as erythritol and glycerol, and it is very difficult to separate and purify ribitol alone from it with good yield. Therefore, there has been desired a method of directly converting a fermentation broth containing ribitol or roughly purified ribitol into L-ribulose without purifying the ribitol in order to industrially produce L-ribulose at a low cost.

Further, even if L-arabinose is used as the raw material instead of ribitol, L-arabinose cannot be said to be inexpensive, and it also provides low yield of L-ribulose.

Also in the third stage, i.e., the reaction of converting L-ribulose into L-ribose, L-ribulose as the raw material must be purified in the conventional techniques. Purified L-ribulose is a very expensive raw material, and it is very difficult to isolate and purify it from the aforementioned liquid containing L-ribulose. Therefore, there has been desired a method of directly converting a fermentation broth containing ribitol or roughly purified ribitol into L-ribulose without purifying the ribitol and further directly converting the L-ribulose contained in the broth containing L-ribulose into L-ribose without purifying the L-ribulose, in order to industrially produce the objective product, L-ribose, at a low cost.

Further, since any method for isolating and purifying L-ribose from an L-ribose containing liquid including a lot of impurities by multiple-step biological reactions is not known at all, it has been necessary to develop an effective method.

DISCLOSURE OF THE INVENTION

The inventors of the present invention assiduously studied in order to solve the aforementioned problems. As a result, they found a method that can efficiently produce non-naturally occurring type L-ribose, which is an important intermediate of drugs and agricultural chemicals, at a low cost by using an inexpensive starting material such as glucose and combining several steps of microbial reactions and purification procedures, and thus accomplished the present invention.

That is, the present invention provides a method for producing L-ribose wherein L-ribose is produced from a saccharide raw material such as glucose as a starting material by using several steps of biological procedures. More specifically, the present invention provides a method for producing L-ribose, which comprises a step of producing ribitol from glucose by using a microorganism having an ability to produce ribitol from a saccharide raw material such as glucose (also referred to as the "first step" hereafter), a step of producing L-ribulose from the ribitol by using a microorganism having an ability to produce L-ribulose from ribitol (also referred to as the "second step" hereafter), and a step of producing L-ribose from the L-ribulose by using a microorganism having an ability to produce L-ribose from the L-ribulose (also referred to as "third step" hereafter).

Furthermore, as preferred embodiments of the present invention, there are provided the aforementioned method that further comprises contacting an L-ribose containing liquid produced by the aforementioned biological procedures with a gel type filtration medium, or adding an organic solvent to the L-ribose containing liquid so that L-ribulose alone should be deposited without depositing unreacted L-ribulose remaining in the reaction mixture.

Hereafter, the present invention will be explained in detail.

The method of the present invention is characterized in that L-ribose is produced starting from a saccharide raw material such as glucose by using several steps of biological procedures, and an example thereof is the method comprising the aforementioned first step, second step and third step. Although the following explanation will be made by exemplifying this method, the present invention is not limited to that method.

The first step of the production method of the present invention is a step of producing ribitol from a saccharide material such as glucose. The microorganism used in the first step is not particularly limited so long as it is a microorganism having an ability to produce ribitol from a saccharide material such as glucose. Preferred examples thereof include microorganisms belonging to the genus Trichosporonoides. More preferred examples include microorganisms belonging to the species *Trichosoporonoides madida, Trichosoporonoides nigrescens, Trichosporonoides oedocephalis, Trichosoporonoides megachillensis* and *Trichosporonoides spathulata*. Further preferred examples include microorganisms belonging to the species *Trichosoporonoides oedocephalis* and *Trichosoporonoides megachillensis*. Examples of the microorganisms belonging to *Trichosoporonoides madida* include, for example, CBS240.79, examples of the microorganisms belonging to *Trichosoporonoides nigrescens* include CBS268.81 and CBS269.81, examples of the microorganisms belonging to *Trichosoporonoides oedocephalis* include CBS568.85 and CBS649.66, examples of the microorganisms belonging to *Trichosoporonoides megachillensis* include CBS567.85, and examples of the microorganisms belonging to *Trichosoporonoides spathulata* include CBS241.79, CBS242.79A and CBS242.79B. These microbial strains can be obtained from Cenatraalbureau voor Schimmelcultures. In addition to wild strains, these strains may be any of mutant strains obtained by UV irradiation, N-methyl-N'-nitrosoguanidine (NTG) treatment, ethyl methanesulfonate (EMS) treatment, nitrous acid treatment, acridine treatment or the like, recombinant strains induced by genetic engineering procedures such as cell fusion and gene recombination and so forth. One of specific examples of the mutant strains is *Trichosporonoides megachillensis* MCI3442 strain. This strain was deposited at the National Institute of Bioscience and Human-Technology, Agency of Industrial Science and Technology, Ministry of International Trade and Industry (postal code: 305-8566, 1–3, Higashi 1-chome, Tsukuba-shi, Ibaraki-ken, Japan) on Jun. 2, 1997, and received an accession number of FERM P-16254. Then, it was transferred to an international deposition under the provisions of Budapest Treaty on Nov. 19, 1997, and received an accession number of FERM BP-6176.

In the first step, one or more kinds of the aforementioned microorganisms are used.

Now, the first step of the method of the present invention will be specifically explained.

In the first step, a microorganism is cultured in a conventional manner by using a saccharide raw material as a carbon source. That is, the microorganism is inoculated to a medium containing 60% (w/v) or less, preferably 20–45%, of the saccharide raw material. As the saccharide raw material, glucose, fructose, sucrose, maltose, glycerol and so forth and mixtures thereof can be mentioned. Among these, glucose is preferred. Form of the saccharide raw material to be used is not particularly limited, and powder, molasses, blackstrap molasses and so forth can be used. The carbon source may be optionally added with carbohydrates such as fructose, alcohols such as glycerol, organic acids and so forth that can be assimilated by the microorganism. The medium further contains a nitrogen source that can be assimilated by the microorganism. As the nitrogen source, any of organic nitrogen sources such as yeast extract, corn steep liquor, NZ amine, triptose, peptone, polypeptone, fish meat extract, meat extract and others, or inorganic nitrogen sources such as sodium nitrate and others, preferably yeast extract and corn steep liquor, can be suitably used. The initial concentration of the nitrogen source contained in the medium is preferably 0.5 to 4.0% for yeast extract, and 1.0 to 8.0% for corn steep liquor. The preferred concentration of the nitrogen source is influenced by the concentration of the saccharide raw material such as glucose. It is also effective to add inorganic ions and vitamins in addition to the aforementioned carbon source and nitrogen source as required. As the inorganic ions, phosphate ions, magnesium ions, iron ions, manganese ions, molybdenum ions and others are used. As the vitamins, thiamine, inositol, pantothenic acid, nicotinamide and so forth can be mentioned. The aforementioned carbon source such as glucose and others, nitrogen source, inorganic ions and vitamins may be supplemented at a suitable time point during the culture as required.

The culture is performed under an aerobic condition. In the present invention, the microorganism may produce erythritol and glycerol as byproducts in addition to ribitol, and it is important to perform sufficient aeration in order to obtain efficient production ratio of ribitol.

The culture temperature is usually 20–37° C., preferably 27–32° C., and it is usually performed for 24 hours to 2 weeks.

The second step of the production method of the present invention is a step of producing L-ribulose from ribitol. The microorganism used in the second step is not particularly limited so long as it is a microorganism having an ability to convert ribitol into L-ribulose under an aerobic reaction condition. However, it is preferably a microorganism having an ability to produce L-ribulose from ribitol and assimilate polyalcohols produced as byproducts other than L-ribulose, more preferably a microorganism belonging to the genus Alcaligenes, Acinetobacter, Agrobacterium, Arthrobacter, Aeromonas, Aureobacterium, Bacillus, Brevibacterium, Klebsiella, Rhizobium, Serratia, Rhodobacter, Corynebacterium, Enterobacter, Gluconobacter, Micrococcus, Paracoccus or Pseudomonas. In particular, a microorganism belonging to the genus Gluconobacter is preferred in view of both of production efficiency of L-ribulose and assimilation property for polyalcohols.

Examples of the microorganism belonging to the genus Gluconobacter used in the present invention include *Gluconobacter frateurii, Gluconobacter oxydans* and so forth. More specific representative strains include *Gluconobacter frateurii* IFO3264 and *Gluconobacter oxydans* IFO 3293.

Examples of the microorganism belonging to the genus Alcaligenes used in the present invention include, for example, *Alcaligenes aquamarinus, Alcaligenes epoxylyticus, Alcaligenes margaritae, Alcaligenes paradoxus* and *Akcaligenes xylosoxidans* subsp. xylosoxidans, and specific strains include *Alcaligenes xylosoxidans* subsp. xylosoxidans IAM12684, *Alcaligenes paradoxus* Biotype I DSM66 and *Alcaligenes paradoxus* Biotype II DSM30162.

Examples of the microorganism belonging to the genus Acinetobacter used in the present invention include, for example, *Acinetobacter tartarogenes*, and specific strains include *Acinetobacter tartarogenes* IFO13644.

Examples of the microorganism belonging to the genus Arthrobacter used in the present invention include, for example, *Arthrobacter atrocyaneus, Arthrobacter pascens, Arthrobacter ramousus* and so forth, and specific strains include *Arthrobacter pascens* IFO12139, *Arthrobacter atrocyaneus* JCM1329, *Arthrobacter ramousus* JCM1334 and so forth.

Examples of the microorganism belonging to the genus Agrobacterium used in the present invention include, for example, *Agrobacterium radiobacter, Agrobacterium tumefaciens* and *Agrobacterium viscosum*, and specific representative strains include *Agrobacterium radiobacter* NRRL B-11291, *Agrobacterium tumefaciens* IAM13129 and *Agrobacterium viscosum* IFO13652.

Examples of the microorganism belonging to the genus Aureobacterium used in the present invention include *Aureobacterium testaceum*, and specific representative strains include *Aureobacterium testaceum* JCM1353.

Examples of the microorganism belonging to the genus Bacillus used in the present invention include, for example, *Bacillus alvei* and *Bacillus coagulans*, and specific representative strains include *Bacillus alvei* IFO3343 and *Bacillus coagulans* AHU 1631.

Examples of the microorganism belonging to the genus Brevibacterium used in the present invention include *Brevibacterium pusillum*, and specific representative strains include *Brevibacterium pusillum* IAM1489.

Examples of the microorganism belonging to the genus Corynebacterium used in the present invention include *Corynebacterium flaccumfaciens*, and specific representative strains include *Corynebacterium flaccumfaciens* ATCC12813.

Examples of the microorganism belonging to the genus Enterobacter used in the present invention include *Enterobacter aerogenes*, and specific representative strains include *Enterobacter aerogenes* IFO13534.

Examples of the microorganism belonging to the genus Klebsiella used in the present invention include, for example, *Klebsiella planticola, Klebsiella oxytoca* and *Klebsiella terrigena*, and specific representative strains include *Klebsiella planticola* NCIB11885, *Klebsiella oxytoca* JCM1665 and *Klebsiella terrigena* JCM1687.

Examples of the microorganism belonging to the genus Micrococcus used in the present invention include, for example, *Micrococcus roseus*, and specific representative strains include *Micrococcus roseus* IFO 3764.

Examples of the microorganism belonging to the genus Paracoccus used in the present invention include, for example, *Paracoccus denitrificans*, and specific representative strains include *Paracoccus denitrificans* IFO13301.

Examples of the microorganism belonging to the genus Pseudomonas used in the present invention include, for example, *Pseudomonas fluorecens* and *Pseudomonas synxantha*, and specific representative strains include *Pseudomonas fluorecens* IFO3903, *Pseudomonas fluorecens*, ATCC13525 and *Pseudomonas synxantha* IAM12356.

Examples of the microorganism belonging to the genus Aeromonas used in the present invention include, for example, *Aeromonas punctata*, and specific strains include *Aeromonas panctata* IFO13288.

Examples of the microorganism belonging to the genus Rhizobium used in the present invention include, for example, *Rhizobium validum* IFO13648.

Examples of the microorganism belonging to the genus Serratia used in the present invention include, for example, *Serratia marcescens*, and specific strains include *Serratia marcescens* ATCC13880.

Examples of the microorganism belonging to the genus Rhodobacter used in the present invention include, for example, *Rhodobacter sphaeroides*, and specific strains include, for example, *Rhodobacter sphaeroides* IFO12203.

The aforementioned microorganisms can be obtained from Institute for Fermentation (IFO), Institute of Applied Microbiology (IAM), Deutsche Samnlung fonMIkroorganismen und Zellkulturen GmbH (DSM), Japan Collection of Microorganisms (JCM), Laboratory of Culture Collection of Microorganisms (AHU), American Type Culture Collection (ATCC) and The National Collections of Industrial and Marin Bacteria (NCIMB).

The aforementioned microorganisms may be, in addition to wild strains, any of mutant strains obtained by UV irradiation, N-methyl-N'-nitrosoguanidine (NTG) treatment, ethyl methanesulfonate (EMS) treatment, nitrous acid treatment, acridine treatment or the like, recombinant strains induced by the genetic engineering procedures such as cell fusion and gene recombination and so forth. Since the aforementioned microorganisms can assimilate polyalcohols produced as byproducts other than ribitol and efficiently convert ribitol into L-ribulose, load in the subsequent steps of separation and purification of L-ribulose can markedly be reduced.

In this step, one or more kinds of the aforementioned microorganisms are used.

The second step of the method of the present invention will be specifically explained hereafter.

Ribitol used in this step may be purified one, or one contained in non-purified or partially purified fermentation broth containing substances other than ribitol. Specifically, the ribitol containing liquid may contain cells, or it may be one in which cells are removed by centrifugation or the like. It may be one in which the microorganism used for the fermentation of ribitol is killed by steam sterilization or the like, or it may be fermentation broth not sterilized. Further, it may be one obtained by purifying the fermentation broth with a simple method. For example, it may be one obtained by removing cells in the fermentation broth and concentrating the broth to be crystallized, or one obtained by partially purifying the fermentation broth by column chromatography or the like. Furthermore, the fermentation broth may be diluted with a suitable buffer such as acetate buffer, phosphate buffer and Tris buffer, or water. Alternatively, it may be concentrated. The microorganism is allowed to act on these fermentation broths under an aerobic condition to produce L-ribulose.

The medium used for the second step of the method of the present invention may be any one so long as it allows growth of the microorganism, induces L-ribulose producing ability, and preferably induces assimilating property for polyalcohols. The medium may be a liquid or solid medium. As the carbon source, there can be mentioned carbohydrates such as glucose, alcohols such as glycerol, organic acids and so forth that can be assimilated by the aforementioned microorganisms, and one or more substances are suitably selected from them. The carbon source is preferably selected from alcohols such as glycerol that induce assimilating property for polyalcohols. The nitrogen source may be any one so long as it can be assimilated by the microorganism. As the nitrogen source, one or more of organic nitrogen sources such as yeast extract, corn steep liquor, NZ amine, triptose, peptone, polypeptone, meat extract, fish meat extract and others, or inorganic nitrogen sources such as sodium nitrate and others are preferably used. The concentrations of the carbon source and the nitrogen source contained in the medium are 0.01 to 20%. It is also effective to add inorganic ions and vitamins in addition to the aforementioned carbon source and nitrogen source as required. As the inorganic ions, phosphate ions, sodium ions, potassium ions, magnesium ions, iron ions, manganese ions, molybdenum ions, calcium ions, cobalt ions and other metal ions are used optionally in combination. As the vitamins, thiamine, inositol, pantothenic acid, nicotinamide and so forth can be mentioned and suitably used. The aforementioned carbon source such as glucose and others, nitrogen source, inorganic ions and vitamins may be supplemented at a suitable time point during the culture as required.

The culture is performed under an aerobic condition. The culture is performed in the temperature range of 4° C. to 50° C., preferably 20° C. to 40° C. The aeration rate is 0.001 vvm to 2 vvm, preferably 0.5 vvm to 1.5 vvm. pH is 2 to 10, preferably 3 to 9.

The culture is usually performed for 10 hours to 2 days.

As the cells used for the second step, the fermentation broth may be used as it is, or those collected by centrifugation or the like may be used. There may be used cells obtained by culture as they are, or processed cells, i.e., those obtained by subjecting cells obtained by culture to a known treatment procedure, such as acetone treatment, lyophilization treatment, surface active agent treatment and toluene treatment, to physically or enzymatically disrupt the cells. Further, it is also possible to use an enzyme fraction having an ability to act on ribitol to produce L-ribulose, which is extracted from cells or processed cells as roughly purified product or purified product. Furthermore, it is also possible to use immobilized cells, processed cells, enzyme fraction and so forth obtained as described above, which are immobilized on polyacrylamide gel, carrageenan gel or the like. Therefore, the term "microorganism" used in the present invention is used as a concept including all of the aforementioned cells, processed cells, enzyme fraction and immobilized materials thereof.

The culture is performed under an aerobic condition. The culture is performed in the reaction temperature range of 4° C. to 50° C., preferably 20° C. to 40° C. pH is 2 to 10, preferably 3 to 8. Although aeration is not required if the medium is sufficiently stirred, it is preferable to perform aeration at a rate of 0.01 vvm to 1 vvm. The amount of the cells used for the reaction is in the range of 0.001% to 50% (weight/volume) in terms of wet cell weight with respect to ribitol-containing fermentation broth. Although the concentration of ribitol is not particularly limited, it is preferably 0.1 to 15%. The concentration of the contained polyalcohols is not also particularly limited. The reaction is usually performed for 1 hour to 2 weeks.

As for L-ribulose obtained by the reaction, the culture broth obtained above may be used as it is without purification, or that separated and purified from the culture broth by a known method may be used for the reaction of the third step. That is, after the culture was completed, microbial cells are first removed by a conventional method such as centrifugation. Prior to the removal of the cells, the cells may be killed by heating the culture broth. The solution from which the cells are removed may be easily purified by using a usual separation method, i.e., chromatography etc. As for industrial operation, it is also possible to perform the separation by quasi mobile phase type chromatography using an ion exchange resin. In the steps of separation and purification, operations for usual purification of saccharides such as desalting and decoloration may also be performed as required.

The third step of the production method of the present invention is a step of preparing L-ribose from L-ribulose. The microorganism used for the third step is not particularly limited, so long as it is a microorganism having an ability to isomerize L-ribulose to produce L-ribose. However, it is preferably a microorganism belonging to the genus Cellulomonas, more preferably a microorganism belonging to the species *Cellulomonas gerida, Cellulomonas biazotea* or *Cellulomonas flavigena*. Examples of the microorganism belonging to *Cellulomonas gerida* include JCM1490, examples of the microorganism belonging to *Cellulomonas biazotea* include ATCC486, and examples of the microorganism belonging to *Cellulomonas flavigena* include ATCC482 etc. These microorganisms can be obtained from Japan Collection of Microorganisms (JCM) and American Type Culture Collection (ATCC).

The aforementioned microorganisms may be, in addition to wild strains, any of mutant strains obtained by UV irradiation, N-methyl-N'-nitrosoguanidine (NTG) treatment, ethyl methanesulfonate (EMS) treatment, nitrous acid treatment, acridine treatment or the like, recombinant strains induced by the genetic engineering procedures such as cell fusion and gene recombination and so forth. Further, instead of the aforementioned microorganisms, an enzyme such as one disclosed in European Patent Publication 807682 (L-ribulose isomerase) may be used.

In this step, one or more kinds of the aforementioned microorganisms are used.

The third step of the method of the present invention will be specifically explained hereafter.

L-ribulose used in this step may be purified, or one contained in non-purified or partially purified fermentation broth containing substances other than L-ribulose. Specifically, the L-ribulose containing liquid may contain cells used in the first and second steps, or it may be one in which cells are removed by centrifugation or the like. It may also be one in which the microorganisms used for the first and second steps are killed by steam sterilization or the like, or it may be fermentation broth not sterilized. Further, it may be one obtained by purifying the fermentation broth by a simple method. For example, it may be one obtained by removing cells in the L-ribulose fermentation broth and concentrating the broth to be crystallized, or one obtained by partially purifying the fermentation broth by column chromatography or the like. Furthermore, the fermentation broth may be diluted with a suitable buffer such as acetate buffer, phosphate buffer and Tris buffer, or water. Alternatively, it may be concentrated. The microorganism is allowed to act on these fermentation broths under an aerobic condition to produce L-ribose.

In the third step of the method of present invention, the microorganism is cultured by a conventional method. That is, as the carbon source, there are used carbohydrates such as glucose, alcohols such as glycerol, organic acids and so forth that can be assimilated by the aforementioned microorganisms, preferably glucose, glycerol, sucrose and so forth, more preferably sucrose. One or more of these substances can be added as the carbon source as required during the culture. The medium further contains a nitrogen source that can be assimilated by the aforementioned microorganisms. As the nitrogen source, any of organic nitrogen sources such as amino acids, yeast extract, soybean peptides, soybean powder, corn steep liquor, NZ amine, triptose, peptone, polypeptone, meat extract, fish meat extract and others, or inorganic nitrogen sources such as sodium nitrate and others, preferably yeast extract, soybean peptides and polypeptone, can be suitably used. It is also effective to add inorganic ions and vitamins in addition to the aforementioned carbon source and nitrogen source as required. As the inorganic ions, phosphate ions, magnesium ions, iron ions, manganese ions, molybdenum ions and others are used. As the vitamins, thiamine, inositol, pantothenic acid, nicotinamide and so forth can be mentioned. The aforementioned carbon source such as sucrose and others, nitrogen source, inorganic ions and vitamins may be supplemented at a suitable time point during the culture as required.

The culture is performed under an aerobic condition. In order to obtain expression of isomerase producing L-ribose from L-ribrose with high activity according to the present invention, aeration is usually performed at a rate of 0.1 vvm to 2.0 vvm, preferably 0.5 vvm to 2.0 vvm.

The culture temperature is usually in the range of 20° C. to 37° C., preferably 27° C. to 32° C. The culture is usually performed for 12 hours to 48 hours.

As the cells used for the isomerization reaction, the culture broth may be used as it is, or those collected by centrifugation or the like may be used. There may be used cells obtained by culture as they are, or processed cells, i.e., those obtained by subjecting cells obtained by culture to a certain known treatment procedure, such as acetone treatment, lyophilization treatment, surface active agent treatment and toluene treatment, to physically or enzymatically disrupt the cells. Further, it is also possible to use an enzyme fraction having an ability to act on L-ribulose to produce L-ribose, which is extracted from cells or processed cells as roughly purified product or purified product. Furthermore, it is also possible to use immobilized cells, processed cells, enzyme fraction and so forth obtained as described above, which are immobilized on polyacrylamide gel, carrageenan gel or the like. Therefore, the term "microorganism" used in the present invention is used as a concept including all of the aforementioned cells, processed cells, enzyme fraction and immobilized materials thereof. In a particularly preferred embodiment, the cells are subjected to toluene treatment. The cells and toluene may be added to the L-ribulose containing liquid. Preferably, the cells are separated form the fermentation broth in which the culture is completed by concentrating the broth, and used for the isomerization reaction.

The isomerization reaction is performed by adding the aforementioned cells or processed cells in an amount of 2 units or more, preferably 6 units or more, per 1 g of ribulose to an L-ribulose aqueous solution adjusted to pH 4–9.5, preferably pH 8.5–9.0, at a temperature of 10° C. to 50° C., preferably 20° C. to 40° C. Since pH of the reaction mixture decreases with progress of the reaction, it is preferable to adjust pH to be around 9.0 with an alkaline solution such as sodium hydroxide solution. Depending on the amount of the cells used, L-ribose and L-ribulose reach equilibrium in several seconds to several days, and the reaction is completed.

The L-ribose produced by the aforementioned three steps is purified. As a result of assiduous studies of the present inventors, L-ribose was separated and purified from the reaction mixture by combining various usual purification techniques according to a certain order and conditions. In the production method of the present invention, L-ribose is obtained by starting from a saccharide material such as glucose through, for example, biological reactions of three steps. When such multiple steps of biological reactions are performed as described above, the obtained L-ribose containing liquid contains, in addition to the unreacted L-ribulose, impurities such as macromolecular substances including proteins derived from the microorganism, salts, organic acids and dihydroxyacetone that are considered to be produced by side reactions, small amount of saccharides and coloring ingredients. It is desirable to remove these impurities at a stage in the purification as early as possible for the subsequent purification.

After the completion of the reaction, the microbial cells are first removed by a conventional method such as centrifugation. Prior to the removal of the cells, inactivation and precipitation of the enzyme may be performed by heating the culture broth in which the culture is completed. It is very effective for the subsequent purification to saturate the liquid with carbon dioxide before or after the removal of the cells. The liquid from which the cells are removed still contains a lot of impurities such as those mentioned above. They can be removed by conventional methods such as chromatography or crystallization. When the amount of the impurities is large, it is preferable to bring the liquid into contact with a gel type filtration medium prior to crystallization to remove a major part of the impurities. While the gel type filtration medium used in the present invention is not particularly limited so long as it can efficiently separate L-ribose and other components, a cation type ion exchanger is preferred, and a cation type ion exchanger of alkali metal or alkaline earth metal type with 4 to 8% of crosslinking degree is more preferred. Specific examples of such an ion exchanger include UBK-530, UBK-535, UBK-550, UBK-555 (all produced by Mitsubishi Chemical) and so forth. It is preferable to perform chromatographic separation by using these.

As specific purification means, for example, the aforementioned gel type filtration medium is made into slurry with deionized water and, after air bubbles are sufficiently eliminated, filled in a separation column. Then, ½ to ¹⁄₁₀₀ volume, preferably ⅕ to ¹⁄₂₀ volume, relative to the volume of the filtration medium filled in the column, of a crude L-ribose containing liquid is fed to the column, and eluted with wafer to fractionate it into an L-ribose fraction and other fractions. This L-ribose fraction can be desalted and decolorized by conventional method, and then crystallized to obtain L-ribose of high purity.

As for industrial operation, further efficient fractionation can be performed by using various known chromatographic separation procedures and quasi moving bed method with a purpose of increasing the separation efficiency and reducing the amount of the eluent water to be used.

In the steps of separation and purification, operations for usual purification of saccharides such as desalting and decoloration may also be performed as required.

In the finally purified L-ribose liquid, unreacted L-ribulose will remain. To obtain L-ribose crystals from this mixture, it is preferable to add an organic solvent to the L-ribose containing liquid to crystallize L-ribose alone without depositing the unreacted L-ribulose. The L-ribose containing liquid is fully concentrated to a Brix degree of preferably 60 or more, more preferably 85 or more, further preferably 90 or more. When this concentrated syrup is left at 4° C., L-ribose alone will be deposited. However, crystallization at such a low temperature takes a long period of time until the deposition, and crystallization ratio is often insufficient. Therefore, the method utilizing the addition of organic acid is preferably used. That is, the aforementioned sufficiently concentrated L-ribose containing syrup is added with an organic solvent in an amount of ½ to 10-fold volume, preferably 1- to 3-fold volume, of the syrup, sufficiently stirred, then added with a trace amount of L-ribose crystals, and left at 4° C. for 24 hours. As the organic solvent to be added, there can be mentioned lower alcohols such as methanol and ethanol, acetone, hexane, acetonitrile, toluene and so forth. Ethanol, 1-propanol and 2-propanol are preferred, and ethanol is more preferred. If chromatographic separation is again performed prior to the crystallization to eliminate L-ribulose in the L-ribose containing liquid, the crystallization ratio will be further increased.

Best Mode for Carrying out the Invention

The present invention will be explained more specifically with reference to the following example. However, the present invention can be added with usual modifications in the art if they do not depart from the scope of the present invention.

EXAMPLE 1

1) Production of Ribitol Fermentation Supernatant

18 L of a medium containing 30% of glucose and 2% of fish meat extract was put into a jar of 30-L volume, and 180 mL of seed culture of *Trichosporonoides megachillensis* (MC13442) was inoculated to the medium. The seed culture was obtained beforehand by culturing the bacterium in a medium containing 30% of glucose and 1% of yeast extract at 30° C. for two days with shaking at 160 rpm using a flask with a baffle. The conditions in the jar were controlled to be 330 rpm, 1 vvm and 30° C., and the culture was performed for 5 days. From the obtained culture broth, 12 L of a transparent culture supernatant was obtained by centrifugation. This fermentation was performed 5 times to obtain 60 L of ribitol fermentation supernatant. The concentrations of the components were 80 g/L for ribitol, 4 g/L for erythritol and 40 g/L for glycerol.

2} Production of Crude L-ribulose Solution

*Gluconobacter frateurii* (IFO3264) was inoculated to two 500-ml flasks with a baffle each containing 100 ml of a medium containing 1% of glycerol, 0.5% of yeast extract and 0.5% of polypeptone. The flasks were mounted on a shaking culture machine that rotated at 160 rpm to perform the culture at 30° C. for one day. 20 L of a medium containing 3% of glycerol, 0.5% of yeast extract and 0.5% of polypeptone was put into a 30-L jar fermenter, and sterilized at 120° C. for 20 minutes. To this, 200 ml of the aforementioned culture broth was inoculated and cultured at 30° C. for one day, while pH was controlled with 5 N sodium hydroxide so that pH should not become 5 or lower. After the completion of the culture, the culture broth was centrifuged to remove the culture supernatant. Thus, cells of *Gluconobacter frateurii* were obtained.

15 L of the ribitol fermentation supernatant produced in the above 1) was put into a 30-L jar fermenter, and added with the obtained cells of the Gluconobacter bacterium. They were allowed to react under conditions of 30° C., aeration at 1 vvm and stirring at 330 rpm. After one day of the reaction, 1 ml of the reaction mixture was centrifuged to remove the cells, and the reaction supernatant was analyzed by high performance liquid chromatography with the conditions shown in the following Table 1. Ribitol was completely converted, and erythritol and glycerol were not detected. The amount of the produced L-ribuloses was 78.2 g/L. Glycerol was converted into dihydroxyacetone, and its produced amount was 23.3 g/L. Although erythritol was converted into erythrulose, it could not be accurately measured since the purity of the standard regent was indefinite.

TABLE 1

Condition of high performance liquid chromatography analysis

Column: MCI GEL CK08E, 8 mm I.D. × 300 mm (produced by Mitsubishi Chemical, Inc.)
Eluent: Distilled water
Flow rate: 1.0 ml/minute
Column temperature: 60° C.
Detector: RI 3) Production of Crude L-ribose Solution The cells to be used for isomerization reaction, which were subjected to a toluene treatment, were added to the L-ribulose containing fermentation broth obtained in the above 2). That is, the L-ribulose containing liquid obtained in 2) was directly subjected to the isomerization reaction in the same jar without being subjected to other treatments such as removal of the cells. Specifically, the L-ribulose containing fermentation broth was adjusted to pH 9.0 with sodium hydroxide aqueous solution when the reaction of 2) was completed, then added with 1 L of cells obtained in the following 4), which were subjected to the toluene treatment, to initiate the isomerization reaction. The jar was controlled to secure a reaction temperature of 28° C. and 112 rpm. pH was mildly controlled to be between 8 to 8.5 with 10 N sodium hydroxide aqueous solution. After 24 hours, the mixing ratio of L-ribose and L-ribulose became about 7:3, and the reaction was completed.

The cells were removed by centrifugation from the liquid in which the reaction was completed to obtain 15.1 L of transparent crude L-ribose solution. The concentrations of the contained components were 39.1 g/L for L-ribose, 16.0 g/L for L-ribulose, and 7 g/L for dihydroxyacetone.

4) Production of Toluene-treated Cells for Isomerization Reaction

Seed culture broth of *Acinetobacter calcoaceticus* DL-28 strain was inoculated at a concentration of 1% to 20 L of a medium containing 2.0 g/L of sucrose, 5.0 g/L of yeast extracts, 5.0 g/L of soybean peptides, 5 g/L of NaCl, 3 g/L of $K_2HPO_4$, 1 g/L of $KH_2PO_4$ and 5 g/L of lysine hydrochloride (pH 7.0) contained in a 30-L jar. The seed culture was obtained beforehand by culturing the bacterium in the same medium contained in a flask with a baffle at 30° C. for 12 hours with shaking at 160 rpm. The conditions in the jar were controlled to be 300 rpm, 1 vvm and 30° C., and the culture was performed for 16 hours. The obtained culture broth in which the culture was completed was centrifuged to remove the culture supernatant to obtain 1.7 L of cell suspension with 10-fold concentration. 27 ml of toluene was added to 1.7 L of the concentrated cells and stirred vigorously for 15 minutes.

Instead of the *Acinetobacter calcoceticus* DL-28 strain, *Cellulomonas gerida* JCM1490, *Cellulomonas biazotea* ATCC486, *Cellulomonas flavigena* ATCC482 and so forth can be used similarly.

5} Purification of Crude L-ribose Solution

The crude ribose solution obtained in 3} was concentrated to a Brix degree of 40 in an evaporator, and subjected to column chromatography.

In the quasi moving bed type chromatographic separation system disclosed in Japanese Patent Laid-open Publication (Kokai) No. 63-158105/1988 (in which a front end and a back end a packed packing bed are connected with a fluid way to make circulation of fluid possible), Na type strong cation exchange resin (DIAION UBK-530, produced by Mitsubishi Chemical Co.) was used as a packing material, and water was used as a desorption agent. A packing bed in which four columns having an inner diameter of 28 mm and a packing layer height of 500 mm were connected in series and packed with 1240 mL in total of the aforementioned packing material was maintained at 65° C., and the fluid was passed through the bed at a volume flow rate of 600 mL/hour. The fluid was fed exclusively from the first column and extracted exclusively from the fourth column, and the separation operation was performed until a static state was attained with the time schedule shown in the following Table 2. The compositions of fractions after the static state was attained are shown in Table 3. The recovery ratio of L-ribose was 81.8%. A major part of the coloring components contained in the raw material was separated into fractions other than that of L-ribose, and the coloration of the L-ribose fraction was markedly reduced compared with that observed before the chromatographic separation.

TABLE 2

Feeding and extraction step: 10.8 minutes
Raw material flow rate: 100 ml/hour
Product fraction flow rate: 120 ml/h
Amount of eluent water flow rate: 600 ml/h
Byproduct flow rate: 580 ml/h
Circulation step: 13.0 minutes
Circulating flow rate: 600 ml/h

TABLE 3

|  | Raw material | L-Ribose fraction | Others |
|---|---|---|---|
| Salts and macromolecules | 40.0 | 1.2 | 67.1 |
| L-Ribulose | 17.7 | 13.8 | 19.8 |
| L-Ribose | 42.3 | 85.0 | 13.1 |

The obtained L-ribose containing fraction was filtered through a hollow fiber type ultrafiltration membrane with an exclusion molecular weight of 10000, then passed through a column filled with a cation exchange resin, and continuously passed through a column filled with an anion exchange resin. Although L-ribose containing solutions undergone the aforementioned desalting and decoloration steps were usually colorless and transparent, some coloring components might remain as the case might be. In such a case, the remaining coloring components were removed by adding a small amount of activated carbon, stirring the solution at 60° C. for 1 hour, and then removing the activated carbon by filtration through diatomaceous earth. The colorless and transparent L-ribose containing solution obtained as described above was concentrated to a Brix degree of 87 in an evaporator, added with ethanol in a volume twice as much as the syrup, added with a small amount of L-ribose crystals as seed crystals, and left stand at 4° C. for 24 hours. Then, L-ribose crystals were deposited. These crystals were washed several times with cold ethanol and exsiccated to obtain crystals with a purity of 99.9%. The crystallization ratio was 70%.

In addition, by evaporating the ethanol from the mother liquor after the crystallization, concentrating it again, adding ethanol and seed crystals, and leaving it stand at a low temperature, second and third crystals could be obtained.

EXAMPLE 2

1) Production of Ribitol Fermentation Supernatant

Culture was performed in the same manner as in Example 1, 1) to obtain 12 L of culture supernatant. The concentrations of the component were 80 g/L for ribitol, 5 g/L for erythritol and 50 g/L for glycerol.

2) Production of Crude L-ribulose Solution

*Gluconobacter frateurii* (IFO3264) was cultured in the same manner as in Example 1 to obtain 18 L of culture broth. After the culture was completed, the culture broth was centrifuged to remove the culture supernatant, and the cells were suspended in 1.8 L of 100 mM phosphate buffer (pH 7.0).

12 L of the ribitol fermentation supernatant obtained in the above 1) was put into a 30-L jar, added with 1.8 L of the Gluconobacter suspension, and allowed to react at 30° C. for 1 day with stirring at 300 rpm and aeration at 1 vvm. The solution after the reaction was centrifuged to remove the cells to obtain 12.5 L of transparent crude L-ribulose solution. The concentration of the produced L-ribulose was 75 g/L, and the concentration of dihydroxyacetone was 29 g/L.

3) Production of Crude L-ribose Solution

*Cellulomonas gerida* (JCM1490) strain was inoculated at a concentration of 1% to 18 L of a medium containing 2.0 g/L of sucrose, 5.0 g/L of yeast extract, 5.0 g/L of soybean peptides, 5 g/L of NaCl, 3 g/L of $K_2HPO_4$, 1 g/L of $KH_2PO_4$ and 15 g/L of L-ribose (pH 7.0) contained in a 30-L jar. The seed culture was obtained beforehand by culturing the bacterium in the same medium contained in a flask with a baffle at 30° C. for 18 hours with shaking at 160 rpm. The conditions in the jar were controlled to be 300 rpm, 1 vvm and 30° C., and the culture was performed for 18 hours. The obtained culture broth in which the culture was completed was centrifuged to collect the cells. The cell pellet was added with 1.8 L of glycine-HCl buffer (50 mM, pH 8.5) and homogenously suspended in the buffer. Then, the suspension was added with 60 mL of toluene and stirred vigorously for 15 minutes. 1.2 L of the toluene-treated cells prepared as described above was added to 12.5 L of the crude L-ribulose solution obtained in 2), and the reaction was performed at 30° C. for 24 hours while gently stirring the mixture so that the mixture should become uniform. During the reaction, pH was controlled to be 8.5 with 1 N NaOH. The obtained mixture after the reaction was centrifuged to remove the cells, and passed through a precision membrane filter with a pore size of 0.22 μm to obtain 12 L of transparent crude L-ribose solution. The concentration of L-ribose was 30 g/L, and the concentration of L-ribulose was 13 g/L.

4) Purification of Crude L-ribose Solution

The crude ribose solution obtained in 3) was concentrated in an evaporator to obtain 2.7 L of crude ribose syrup. The concentration of this syrup was 63 in terms of Brix degree. The ratios with respect to solid content were about 38% for L-ribose, and 15% for L-ribulose, in terms of peak areas obtained in HPLC. This syrup was subjected to column chromatography. That is, four columns each filled with 320 mL of ion exchange resin UBK-550 (produced by Mitsubishi Chemical Co.) were connected in series. In a state that the columns were maintained at 65° C., 64 mL of the crude ribose syrup was supplied at a flow rate of 600 mL/hour from one end of the columns. Then, wafer was fed at a flow rate of 600 mL/hour to transfer the syrup to the other end while developing and separating the syrup in the column. When 78 minutes passed after the start of the feeding of water, the desired L-ribose began to be eluted. After further 12 minutes, collection of the eluted solution as an L-ribose containing fraction was started. When 124 minutes passed after the start of the feeding of water, the elution of L-ribose substantially ceased, and therefore collection of samples was finished. The ratios with respect to the solid content in this L-ribose containing fraction were 80% for L-ribose and 14% for L-ribulose, in terms of peak areas obtained in HPLC. The recovery ratio of L-ribose was 80.1%. When this L-ribose fraction was subjected to the same desalting and decolorization treatments as Example 1, concentrated to a Brix degree of 90, and left stand at 4° C. for 1 month, L-ribose crystals were deposited. These crystals were washed several times with cold alcohol or the like, and exsiccated to obtain crystals with a purity of 99%.

EXAMPLE 3

The L-ribose containing fraction obtained by the quasi moving bed method in Example 1 was further purified by column chromatography.

The same chromatographic separation system as Example 1 was used, and a Ca type strong cation exchange resin (DIAION UBK-555, produced by Mitsubishi Chemical Co.) was used as the packing agent. A separation operation was performed until a static state was attained with the time schedule shown in the following Table 4. The compositions of fractions after the static state was attained are shown in Table 5. The recovery ratio of L-ribose was 72.4%.

TABLE 4

Feeding and extraction step: 9.6 minutes
Raw material flow rate: 75 ml/hour
Product fraction flow rate: 244 ml/h
Amount of eluent water flow rate: 600 ml/h
Byproduct flow rate: 431 ml/h
Circulation step: 23.0 minutes
Circulating flow rate: 600 ml/h

TABLE 5

|  | Raw material | L-Ribose fraction | Others |
|---|---|---|---|
| Salts and macromolecules | 1.2 | 0.0 | 3.2 |
| L-Ribulose | 13.8 | 2.0 | 33.5 |
| L-Ribose | 85.0 | 98.0 | 63.2 |

When the obtained L-ribose fraction was subjected to desalting and decoloration treatments in the same manner as in Example 1, concentrated to a Brix degree of 87, added with 2-fold volume of 2-propanol and a trace amount of L-ribose crystals, and stirred at 4° C. for 12 hours, L-ribose crystals of 99.5% purity was obtained.

The contents of saccharides including ribitol contained in the culture supernatants obtained in each example were measured by high performance liquid chromatography with the conditions shown in the following Table 6. The retention times for the saccharides were 10.57 minutes for glucose, 12.22 minutes for ribitol, 13.36 minutes for erythritol and 15.09 minutes for glycerol under the following analysis condition A, and 22.8 minutes for L-ribulose and 24.0 minutes for L-ribose under the following analysis condition B.

TABLE 6

High performance liquid chromatography analysis condition A

Column: MCI GEL CK08EH, 8 mm I.D. × 300 mm (produced by Mitsubishi Chemical, Inc.)
Eluent: 1 N phosphoric acid aqueous solution
Flow rate: 0.6 ml/minute
Column temperature: 50° C.
Detector: RI High performance liquid chromatography analysis condition B Column: MCI GEL CK08EC, 8 mm I.D. × 300 mm (produced by Mitsubishi Chemical, Inc.)
Eluent: water
Flow rate: 0.6 ml/minute
Column temperature: 75° C.
Detector: RI Industrial Applicability According to the present invention, L-ribose can be-efficiently produced through several steps of biological reactions starting from an inexpensive saccharide material such as glucose.

What is claimed is:

1. A method for producing L-ribose, comprising:
   producing ribitol from a saccharide raw material by using a microorganism having an ability to produce ribitol from a saccharide raw material, wherein the saccharide raw material is selected from the group consisting of glucose, fructose, sucrose, maltose and glycerol,
   producing L-ribulose from the ribitol by using a microorganism having an ability to produce L-ribulose from ribitol, and
   producing L-ribose from the L-ribulose by using a microorganism having an ability to produce L-ribose from L-ribulose.

2. The method according to claim 1, wherein the saccharide raw material is glucose.

3. The method according to claim 2, wherein the microorganism having an ability to produce ribitol from glucose belongs to the genus Trichosporonoides.

4. The method according to claim 3, wherein the microorganism is selected from the group consisting of *Trichosoporonoides madida*, *Trichosoporonoides nigrescens*, *Trichosoporonoides oedocephalis*, *Trichosoporonoides megachillensis* and *Trichosoporonoides spathulata*.

5. The method according to claim 3, wherein the microorganism is selected from the group consisting of *Trichosoporonoides oedocephalis* and *Trichosoporonoides megachillensis*.

6. The method according to claim 4, wherein the microorganism belonging to the genus Trichosporonoides is selected from the group consisting of *Trichosoporonoides madida* CBS240.79, *Trichosoporonoides nigrescens* CBS268.81 and CBS269.81, *Trichosoporonoides oedocephalis* CBS568.85 and CBS649.66, *Trichosoporonoides megachillensis* CBS567.85 and FERM BP-6176, *Trichosoporonoides spathulata* CBS241.79, CBS242.79A and CBS242.79B.

7. The method according to claim 5, wherein the microorganism belonging to the genus Trichosporonoides is selected from the group consisting of *Trichosporonoides oedocephalis* CBS568.85, *Trichosoporonoides megachillensis* CBS567.85 and FERM BP-6176.

8. The method according to claim 1 or 3, wherein the microorganism having an ability to produce L-ribulose from ribitol is a microorganism having an ability to assimilate polyalcohols other than ribitol, which are produced as byproduct.

9. The method according to claim 1 or 3, wherein the microorganism having an ability to produce L-ribulose from ribitol is selected from the group consisting of microorganisms belonging to genus Alcaligenes, Acinetobacter, Agrobacterium, Arthrobacter, Aeromonas, Aureobacterium, Bacillus, Brevibacterium, Klebsiella, Rhizobium, Serratia, Rhodobacter, Corynebacterium, Enterobacter, Gluconobacter, Micrococcus, Paracoccus and Pseudomonas.

10. The method according to claim 8, wherein the microorganism belongs to the genus Gluconobacter.

11. The method according to claim 10, wherein the microorganism is selected from the group consisting of microorganisms belonging to *Gluconobacter frateurii* and *Gluconobacter oxyaans*.

12. The method according to claim 11, wherein the microorganism is selected from the group consisting of *Gluconobacter frateurii* IFO3264 and *Gluconobacter oxydans* IFO3293.

13. The method according to claim 1, wherein ribitol is one contained in an unpurified fermentation broth containing substances other than ribitol or the fermentation broth that is partially purified.

14. The method according to claim 1 or 3, wherein the microorganism having an ability to produce L-ribose from L-ribulose is selected from the group consisting of microorganisms belonging to the genus Cellulomonas.

15. The method according to claim 14, wherein the microorganism is selected from the group consisting of *Cellulomonas gerida*, *Cellulomonas biazotea* and *Cellulomonas flavigena*.

16. The method according to claim 15, wherein the microorganism is selected from the group consisting of *Cellulomonas gerida* JCM 1490, *Cellulomonas biazotea* ATCC486 and *Cellulomonas flavigena* ATCC482.

17. The method according to claim 14, wherein the L-ribulose is one contained in an unpurified fermentation broth containing substances other than L-ribulose or the fermentation broth that is partially purified.

18. The method according to claim 1, wherein a reaction mixture containing the produced L-ribose is brought into contact with a gel type filtration medium.

19. The method according to claim 18, wherein L-ribose is chromatographically separated by contact with a gel type filtration medium.

20. The method according to claim 19, wherein the gel type filtration medium is a cation type ion exchanger.

21. The method according to claim 1, wherein an organic solvent is added to a reaction mixture containing the produced L-ribose so that L-ribose alone should be deposited without depositing unreacted L-ribulose remaining in the reaction mixture.

22. The method according to claim 21, wherein the organic solvent is a lower alcohol, acetone, hexane, acetonitrile or toluene.

23. The method according to claim 8, wherein ribitol is one contained in an unpurified fermentation broth containing substances other than ribitol or the fermentation broth that is partially purified.

24. The method according to claim 8, wherein the microorganism having an ability to produce L-ribose from L-ribulose is selected from the group consisting of microorganisms belonging to the genus Cellulomonas and Acinetobacter.

25. The method according to claim 9, wherein the microorganism having an ability to produce L-ribose from L-ribulose is selected from the group consisting of microorganisms belonging to the genus Cellulomonas and Acinetobacter.

* * * * *

UNITED STATES PATENT AND TRADEMARK OFFICE
CERTIFICATE OF CORRECTION

PATENT NO. : 6,348,326 B1
DATED : February 19, 2002
INVENTOR(S) : Tomoko Kawaguchi et al.

It is certified that error appears in the above-identified patent and that said Letters Patent is hereby corrected as shown below:

Column 3,
Line 19, change "*Trichosoporonoides*" to -- *Trichosporonoides* --, and change "*Trichosopo-*" to -- *Trichospo-* --;
Line 23, change "*Trichosoporonoides*" to -- *Trichosporonoides* --;
Lines 25, 27, 29 and 31, change "*Trichosopo-*" to -- *Trichospo-* --;
Line 33, change "*Trichosoporonoides*" to -- *Trichosporonoides* --.

Column 4,
Line 60, change "*Akcaligenes*" to -- *Alcaligenes* --.

Column 5,
Line 62, change "*panctata*" to -- *punctata* --;

Column 6,
Line 9, change "Samnlung fonMlkroorgan-" to -- Sammlung vonMikroorgan- --;
Line 14, change "Marin" to -- Marine --.

Column 9,
Line 13, change "L-ribrose" to -- L-ribulose --.

Column 11,
Line 36, change "2}" to -- 2) --.

Column 12,
Line 61, change "5}" to -- 5) --;
Line 62, change "3}" to -- 3) --.

Column 16,
Line 47, change "*soporonoides*" to -- *sporonoides* --; and change "*Trichosoporonoides*" to -- *Trichosporonoides* --;
Line 48, change "*chosoporonoides*" to -- *chosporonoides* --; and change "*Trichosoporonoides*" to -- *Trichosporonoides* --.
Line 52, change "*soporonoides*" to -- *sporonoides* --.
Lines 57 and 59, change "*Trichosoporonoides*" to -- *Trichosporonoides* --;
Line 60, "*Trichosopo-*" to -- *Trichospo-* --.

UNITED STATES PATENT AND TRADEMARK OFFICE
CERTIFICATE OF CORRECTION

PATENT NO. : 6,348,326 B1
DATED : February 19, 2002
INVENTOR(S) : Tomoko Kawaguchi et al.

It is certified that error appears in the above-identified patent and that said Letters Patent is hereby corrected as shown below:

Column 16 cont'd,
Line 66, change "*Trichosoporonoides*" to -- *Trichosporonoides* --.
Line 66, change "*oxyaans*" to -- *oxydans* --.

Signed and Sealed this

Twenty-eighth Day of January, 2003

JAMES E. ROGAN
*Director of the United States Patent and Trademark Office*